United States Patent
Nakasawa et al.

(10) Patent No.: US 10,094,841 B2
(45) Date of Patent: Oct. 9, 2018

(54) AUTOMATIC ANALYZER

(75) Inventors: Takashi Nakasawa, Tokyo (JP); Yoichi Aruga, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 250 days.

(21) Appl. No.: 14/236,670

(22) PCT Filed: Jul. 9, 2012

(86) PCT No.: PCT/JP2012/067418
§ 371 (c)(1),
(2), (4) Date: Feb. 3, 2014

(87) PCT Pub. No.: WO2013/042431
PCT Pub. Date: Mar. 28, 2013

(65) Prior Publication Data
US 2014/0170027 A1    Jun. 19, 2014

(30) Foreign Application Priority Data

Sep. 21, 2011  (JP) .................................. 2011-205496

(51) Int. Cl.
G01N 35/00 (2006.01)
(52) U.S. Cl.
CPC ... G01N 35/00693 (2013.01); G01N 35/0092 (2013.01); *G01N 2035/0097* (2013.01)
(58) Field of Classification Search
None
See application file for complete search history.

(56) References Cited

U.S. PATENT DOCUMENTS

| | | | | |
|---|---|---|---|---|
| 5,316,726 | A * | 5/1994 | Babson | G01N 35/0095 356/418 |
| 5,741,461 | A * | 4/1998 | Takahashi | G01N 35/00594 422/64 |
| 6,080,364 | A * | 6/2000 | Mimura | G01N 35/00712 422/63 |
| 2002/0116132 | A1* | 8/2002 | Rhett | G01N 1/312 702/19 |
| 2002/0147515 | A1* | 10/2002 | Fava | G01N 35/00603 700/95 |
| 2004/0181343 | A1* | 9/2004 | Wigstrom | B01L 3/5027 702/19 |

(Continued)

FOREIGN PATENT DOCUMENTS

JP  2007-292525 A  11/2007
JP  2008-064680 A  3/2008

(Continued)

*Primary Examiner* — Benjamin R Whatley
(74) *Attorney, Agent, or Firm* — Mattingly & Malur, PC

(57) ABSTRACT

A control unit outputs measurement status information including the time up to the completion of creation of the calibration curve for each of the desired measurement items to a display unit. The output/display of the calibration curve data measurement status for each of the items enables the operator to be aware of information about a failure to set a standard solution or to request the setting of the standard solution and to recognize how long he or she will need to wait until the creation of the calibration curve begins. The operator can therefore know what can be done while waiting, thereby improving job efficiency.

7 Claims, 9 Drawing Sheets

(56) References Cited

U.S. PATENT DOCUMENTS

| | | | | |
|---|---|---|---|---|
| 2004/0202577 | A1* | 10/2004 | McNeil | G01N 33/5302 422/82.08 |
| 2005/0227360 | A1* | 10/2005 | Devlin, Sr. | G01N 35/0092 436/45 |
| 2006/0027490 | A1* | 2/2006 | DeMarco | G01N 30/88 210/198.2 |
| 2006/0046298 | A1* | 3/2006 | Key | G01N 1/30 436/43 |
| 2006/0178776 | A1* | 8/2006 | Feingold | G01N 1/312 700/245 |
| 2007/0077643 | A1* | 4/2007 | Nakamura | G01N 35/00722 435/286.1 |
| 2007/0154970 | A1* | 7/2007 | Buechler | G01N 33/54306 435/7.92 |
| 2008/0020469 | A1* | 1/2008 | Barnes | G01N 35/0092 436/46 |
| 2008/0056939 | A1* | 3/2008 | Awata | G01N 35/00663 422/50 |
| 2008/0230697 | A1* | 9/2008 | Tanimoto | G01N 23/225 250/310 |
| 2008/0240988 | A1* | 10/2008 | Wakamiya | G01N 35/00693 422/68.1 |
| 2009/0004057 | A1 | 1/2009 | Sato | |
| 2009/0081794 | A1* | 3/2009 | Wakamiya | G01N 35/0092 436/43 |
| 2009/0142231 | A1* | 6/2009 | Shibuya | G01N 35/00663 422/68.1 |
| 2009/0214385 | A1* | 8/2009 | Mori | G01N 35/10 422/63 |
| 2009/0269242 | A1* | 10/2009 | Nozawa | G01N 35/00693 422/68.1 |
| 2010/0209298 | A1* | 8/2010 | Kalra | B01L 3/508 422/63 |
| 2010/0250174 | A1* | 9/2010 | Tokunaga | G01N 35/0092 702/83 |
| 2011/0169836 | A1* | 7/2011 | Orihashi | G01N 35/00722 345/440 |
| 2011/0259129 | A1* | 10/2011 | Murata | G01N 35/00693 73/866.3 |
| 2011/0301917 | A1* | 12/2011 | Kamihara | G01N 35/00693 702/179 |
| 2012/0000268 | A1* | 1/2012 | Li | G01N 35/00613 73/1.01 |
| 2012/0004857 | A1* | 1/2012 | Yamato | G01N 35/0092 702/19 |

FOREIGN PATENT DOCUMENTS

| | | |
|---|---|---|
| JP | 2009-008611 A | 1/2009 |
| JP | 2010-151707 A | 7/2010 |

* cited by examiner

FIG. 2

| ROUTINE OPERATIONS | REAGENT MANAGEMENT | CALIBRATION | ACCURACY CONTROL | UTILITIES |

| MEASUREMENT REQUEST | MEASUREMENT STATUS | STANDARD SOLUTION MEASUREMENT STATUS |

Table 24:

| STATUS | ITEM NAME | LOCATION | USAGE STATUS | EXECUTION METHOD | RESIDUAL TIME |
|--------|-----------|----------|--------------|------------------|---------------|
|        | TestA     | M1-1     | IN USE       | 2-POINT          |               |
|        | TestA     | M1-2     | STANDBY      | BLANK            |               |
| S      | TestA     | M2-1     | IN USE       |                  |               |
| F      | TestA     | M2-2     | STANDBY      | BLANK            | 4 min         |
| P      | TestB     | M1-4     | IN USE       | ALL-POINT        |               |
|        | TestC     | M1-5     | IN USE       |                  |               |

P : UNDER PROCESS
S : CALIBRATION SUCCEEDED
F : CALIBRATION FAILED

Table 25:

| STATUS | STANDARD SOLUTION | LOCATION | ANALYSIS START TIME | RESIDUAL TIME |
|--------|-------------------|----------|---------------------|---------------|
|        | STD1              | S0004-1  |                     |               |
|        | STD1              | S0004-1  |                     |               |
|        | STD2              | S0006-1  |                     |               |
|        | STD2              | S0006-1  |                     |               |
|        | STD3              | S0006-2  |                     |               |
|        | STD3              | S0006-3  |                     |               |
|        | STD4              | S0006-3  |                     |               |
|        | STD4              | S0006-4  |                     |               |
|        | STD5              | S0006-4  |                     |               |
|        | STD5              | S0006-4  |                     |               |

P : UNDER PROCESS
S : MEASUREMENT SUCCEEDED
F : MEASUREMENT FAILED

FIG. 3

Tabs: ROUTINE OPERATIONS | REAGENT MANAGEMENT | MEASUREMENT STATUS | CALIBRATION | ACCURACY CONTROL | UTILITIES Sub-tabs: MEASUREMENT REQUEST | STANDARD SOLUTION MEASUREMENT STATUS Table 24:

| STATUS | ITEM NAME | LOCATION | USAGE STATUS | EXECUTION METHOD | RESIDUAL TIME |
|---|---|---|---|---|---|
|  | TestA | M1-1 | IN USE | 2-POINT |  |
|  | TestA | M1-2 | STANDBY | BLANK |  |
| S | TestA | M2-1 | IN USE |  |  |
| F | TestA | M2-2 | STANDBY | BLANK |  |
| P | TestB | M1-4 | IN USE | BLANK | 4 min |
|  | TestC | M1-5 | IN USE | BLANK? |  |

P : UNDER PROCESS
S : CALIBRATION SUCCEEDED
F : CALIBRATION FAILED

Table 25:

| STATUS | STANDARD SOLUTION | LOCATION | ANALYSIS START TIME | RESIDUAL TIME |
|---|---|---|---|---|
|  | STD1 | S0004-1 |  |  |
|  | STD1 | S0004-1 |  |  |

P : UNDER PROCESS
S : MEASUREMENT SUCCEEDED
F : MEASUREMENT FAILED

FIG. 4

| | ROUTINE OPERATIONS | REAGENT MANAGEMENT | CALIBRATION | ACCURACY CONTROL | UTILITIES |

MEASUREMENT REQUEST | MEASUREMENT STATUS | STANDARD SOLUTION MEASUREMENT STATUS

| STATUS | ITEM NAME | LOCATION | USAGE STATUS | EXECUTION METHOD | RESIDUAL TIME |
|---|---|---|---|---|---|
| | TestA | M1-1 | IN USE | 2-POINT | |
| S | TestA | M1-2 | STANDBY | BLANK | |
| F | TestA | M2-1 | IN USE | | |
| | TestA | M2-2 | STANDBY | BLANK | |
| P | TestB | M1-4 | IN USE | | 4 min |
| | TestC | M1-5 | IN USE | ALL-POINT | |

P : UNDER PROCESS
S : CALIBRATION SUCCEEDED
F : CALIBRATION FAILED

| STATUS | STANDARD SOLUTION | LOCATION | ANALYSIS START TIME | RESIDUAL TIME |
|---|---|---|---|---|
| P | STD1 | S0004-1 | 01/01 11:57 | 7 min |
| P | STD1 | S0004-1 | 01/01 11:57 | 7 min |
| P | STD2 | S0006-1 | 01/01 11:59 | 9 min |
| P | STD3 | S0006-1 | 01/01 11:59 | 9 min |
| P | STD3 | S0006-2 | 01/01 12:00 | 10 min |
| P | STD4 | S0006-2 | 01/01 12:00 | 10 min |
| | STD4 | S0006-3 | | |
| | STD5 | S0006-4 | | |
| | STD5 | S0006-4 | | |

P : UNDER PROCESS
S : MEASUREMENT SUCCEEDED
F : MEASUREMENT FAILED

FIG. 5

ROUTINE OPERATIONS | REAGENT MANAGEMENT | MEASUREMENT STATUS | CALIBRATION | ACCURACY CONTROL | UTILITIES

MEASUREMENT REQUEST | STANDARD SOLUTION MEASUREMENT STATUS

| STATUS | ITEM NAME | LOCATION | USAGE STATUS | EXECUTION METHOD | RESIDUAL TIME |
|---|---|---|---|---|---|
|  | TestA | M1-1 | IN USE | 2-POINT |  |
| S | TestA | M1-2 | STANDBY | BLANK |  |
| F | TestA | M2-1 | IN USE |  |  |
| P | TestA | M2-2 | STANDBY | BLANK |  |
| P | TestB | M1-4 | IN USE | BLANK | 4 min |
| P | TestC | M1-5 | IN USE | ALL-POINT | 10 min |

P : UNDER PROCESS
S : CALIBRATION SUCCEEDED
F : CALIBRATION FAILED

| STATUS | STANDARD SOLUTION | LOCATION | ANALYSIS START TIME | RESIDUAL TIME |
|---|---|---|---|---|
| P | STD1 | S0004-1 | 01/01 11:57 | 6 min |
| P | STD1 | S0004-1 | 01/01 11:57 | 6 min |
| P | STD2 | S0006-1 | 01/01 11:59 | 8 min |
| P | STD2 | S0006-1 | 01/01 11:59 | 8 min |
| P | STD3 | S0006-2 | 01/01 12:00 | 9 min |
| P | STD3 | S0006-3 | 01/01 12:00 | 9 min |
| P | STD4 | S0006-3 | 01/01 12:00 | 9 min |
| P | STD4 | S0006-4 | 01/01 12:01 | 10 min |
| P | STD5 | S0006-4 | 01/01 12:01 | 10 min |

P : UNDER PROCESS
S : MEASUREMENT SUCCEEDED
F : MEASUREMENT FAILED

FIG. 6

| ROUTINE OPERATIONS | REAGENT MANAGEMENT | CALIBRATION | ACCURACY CONTROL | UTILITIES |

MEASUREMENT REQUEST | MEASUREMENT STATUS | STANDARD SOLUTION MEASUREMENT STATUS

| STATUS | ITEM NAME | LOCATION | USAGE STATUS | EXECUTION METHOD | RESIDUAL TIME |
|---|---|---|---|---|---|
|  | TestA | M1-1 | IN USE | 2-POINT |  |
| S | TestA | M1-2 | STANDBY | BLANK |  |
| F | TestA | M2-1 | IN USE |  |  |
| P | TestA | M2-2 | STANDBY | BLANK | 4 min |
|  | TestB | M1-4 | IN USE |  |  |
| F | TestC | M1-5 | IN USE | ALL-POINT |  |

P : UNDER PROCESS
S : CALIBRATION SUCCEEDED
F : CALIBRATION FAILED

| STATUS | STANDARD SOLUTION | LOCATION | ANALYSIS START TIME | RESIDUAL TIME |
|---|---|---|---|---|
| P | STD1 | S0004-1 | 01/01 11:57 | 6 min |
| P | STD1 | S0004-1 | 01/01 11:57 | 6 min |
| P | STD2 | S0006-1 | 01/01 11:59 | 8 min |
| P | STD2 | S0006-1 | 01/01 11:59 | 8 min |
| P | STD3 | S0006-2 | 01/01 12:00 | 9 min |
| P | STD3 | S0006-2 | 01/01 12:00 | 9 min |
| F | STD4 | S0006-3 |  |  |
| F | STD4 | S0006-3 |  |  |
| P | STD5 | S0006-4 | 01/01 12:01 | 10 min |
| P | STD5 | S0006-4 | 01/01 12:01 | 10 min |

P : UNDER PROCESS
S : MEASUREMENT SUCCEEDED
F : MEASUREMENT FAILED

FIG. 7

ROUTINE OPERATIONS | REAGENT MANAGEMENT | CALIBRATION | ACCURACY CONTROL | UTILITIES

MEASUREMENT REQUEST | MEASUREMENT STATUS | STANDARD SOLUTION MEASUREMENT STATUS

| STATUS | ITEM NAME | LOCATION | USAGE STATUS | EXECUTION METHOD | RESIDUAL TIME |
|---|---|---|---|---|---|
|  | TestA | M1-1 | IN USE | 2-POINT |  |
| S | TestA | M1-2 | STANDBY | BLANK |  |
| F | TestA | M2-1 | IN USE |  |  |
| P | TestB | M2-2 | STANDBY |  |  |
|  | TestB | M1-4 | IN USE | BLANK | 4 min |
| F | TestC | M1-5 | IN USE | ALL-POINT |  |

P : UNDER PROCESS
S : CALIBRATION SUCCEEDED
F : CALIBRATION FAILED

| STATUS | STANDARD SOLUTION | LOCATION | ANALYSIS START TIME | RESIDUAL TIME |
|---|---|---|---|---|
| P | STD1 | S0004-1 | 01/01 11:57 | 6 min |
| P | STD1 | S0004-1 | 01/01 11:57 | 6 min |
| P | STD2 | S0006-1 | 01/01 11:59 | 8 min |
| P | STD2 | S0006-2 | 01/01 11:59 | 8 min |
| P | STD3 | S0006-2 | 01/01 12:00 | 9 min |
| P | STD3 | S0006-3 | 01/01 12:00 | 9 min |
| F | STD4 | S0006-3 | 01/01 12:00 | 9 min |
| P | STD4 | S0006-4 | 01/01 12:01 | 10 min |
| P | STD5 | S0006-4 | 01/01 12:01 | 10 min |
| P | STD5 | S0006-4 | 01/01 12:01 | 10 min |

P : UNDER PROCESS
S : MEASUREMENT SUCCEEDED
F : MEASUREMENT FAILED

FIG. 8

| ROUTINE OPERATIONS | REAGENT MANAGEMENT | MEASUREMENT STATUS | CALIBRATION | ACCURACY CONTROL | UTILITIES |

MEASUREMENT REQUEST | STANDARD SOLUTION MEASUREMENT STATUS — 23

24

| STATUS | ITEM NAME | LOCATION | USAGE STATUS | EXECUTION METHOD | RESIDUAL TIME |
|---|---|---|---|---|---|
|  | TestA | M1-1 | IN USE | 2-POINT |  |
| S | TestA | M1-2 | STANDBY | BLANK |  |
| F | TestA | M2-1 | IN USE |  |  |
|  | TestA | M2-2 | STANDBY |  |  |
| P | TestB | M1-4 | IN USE | BLANK | 4 min |
| P | TestC | M1-5 | IN USE | ALL-POINT | 2 min |

P : UNDER PROCESS
S : CALIBRATION SUCCEEDED
F : CALIBRATION FAILED

25

| STATUS | STANDARD SOLUTION | LOCATION | ANALYSIS START TIME | RESIDUAL TIME |
|---|---|---|---|---|
| S | STD1 | S0004-1 | 01/01 11:57 |  |
| S | STD1 | S0004-1 | 01/01 11:57 |  |
| S | STD2 | S0006-1 | 01/01 11:59 |  |
| S | STD2 | S0006-2 | 01/01 11:59 |  |
| S | STD3 | S0006-2 | 01/01 12:00 |  |
| P | STD3 | S0006-3 | 01/01 12:00 | 1 min |
| P | STD4 | S0006-3 | 01/01 12:00 | 1 min |
| P | STD4 | S0006-4 | 01/01 12:01 | 2 min |
| P | STD5 | S0006-4 | 01/01 12:01 | 2 min |

P : UNDER PROCESS
S : MEASUREMENT SUCCEEDED
F : MEASUREMENT FAILED

FIG. 9

| | | | | | RESIDUAL TIME |
|---|---|---|---|---|---|
| STATUS | ITEM NAME | LOCATION | USAGE STATUS | EXECUTION METHOD | RESIDUAL TIME |
| | TestA | M1-1 | IN USE | 2-POINT | |
| S | TestA | M1-2 | STANDBY | BLANK | |
| F | TestA | M2-1 | IN USE | | |
| P | TestA | M2-2 | STANDBY | BLANK | 4 min |
| S | TestB | M1-4 | IN USE | ALL-POINT | |
| | TestC | M1-5 | IN USE | | |

P : UNDER PROCESS
S : CALIBRATION SUCCEEDED
F : CALIBRATION FAILED

| STATUS | STANDARD SOLUTION | LOCATION | ANALYSIS START TIME | RESIDUAL TIME |
|---|---|---|---|---|
| S | STD1 | S0004-1 | 01/01 11:57 | |
| S | STD1 | S0004-1 | 01/01 11:57 | |
| S | STD2 | S0006-1 | 01/01 11:59 | |
| S | STD2 | S0006-1 | 01/01 11:59 | |
| S | STD3 | S0006-2 | 01/01 12:00 | |
| S | STD3 | S0006-2 | 01/01 12:00 | |
| S | STD4 | S0006-3 | 01/01 12:00 | |
| S | STD4 | S0006-3 | 01/01 12:00 | |
| S | STD5 | S0006-4 | 01/01 12:01 | |
| S | STD5 | S0006-4 | 01/01 12:01 | |

P : UNDER PROCESS
S : MEASUREMENT SUCCEEDED
F : MEASUREMENT FAILED

Tabs: ROUTINE OPERATIONS | REAGENT MANAGEMENT | MEASUREMENT STATUS | CALIBRATION | ACCURACY CONTROL | UTILITIES
Sub-tab: MEASUREMENT REQUEST | STANDARD SOLUTION MEASUREMENT STATUS ID

US 10,094,841 B2

AUTOMATIC ANALYZER

TECHNICAL FIELD

The present invention relates generally to automatic analyzers for clinical laboratory tests used for qualitative/quantitative analysis on such biological samples as of blood and urine, more particularly to an automatic analyzer having a function that creates a calibration curve for computing concentrations.

BACKGROUND ART

Automatic analyzers for clinical laboratory tests are used to measure specific constituents contained in such biological samples as of blood and urine. The operation of a general automatic analyzer is to dispense a sample and reagent into a reaction vessel via respective special nozzles. After stirring the sample and reagent and causing reactions between these substances for a fixed time, the automatic analyzer computes a concentration of a desired item from the information obtained from a resulting reaction solution such as absorbance and the amount of light generated by the analyte. The computation of such a concentration uses a calibration curve, in which an approximate amount of light absorbed or generated per unit concentration is adopted as an index. A way to compute concentration using absorbance in order to create a calibration curve is discussed below by way of example. First, a plurality of absorbance values per unit concentration are measured using several standard solutions of a predetermined concentration, and a relationship between the measured concentration and absorbance values is plotted. Then, the plotted data points are connected using regression equations/formulas for linearity or nonlinearity, thereby creating a calibration curve.

The number of standard solutions measured prior to the creation of the calibration curve differs depending on the item. These standard solutions may have a plurality of items in common with a solution, which makes it difficult for a user of the apparatus to accurately understand how long it will take till the measurement for a desired item becomes measurable.

Since a plurality of standard solutions need to be used, failure to request the measurement of even one of the standard solutions, or failure to set even one standard solution in the apparatus would result in failing to create a calibration curve, which would then make it necessary to request the measurement once again. This is greatly inconvenient.

Patent Document 1 as JP-2010-151707-A below discloses an example of an analyzer having a function that makes a GUI screen of a residual waiting time required until the analyzer can start measuring each of a plurality of standard solutions (hereinafter, this time may be referred to simply as the residual time). The creation of a calibration curve requires prior acquisition of measurement results on all the standard solutions necessary for a particular item. A plurality of standard solutions, however, might have a different number of items allocated to each of the standard solutions or might not be adjacent to each other. This makes it less beneficial to display the residual time up to the start of the measurement for each of the standard solutions since a total residual time for all the standard solutions needs to be confirmed and calculated before the time up to the acquisition of all desired items. Additionally, whether the necessary standard solutions have been measured needs to be confirmed for each of the standard solutions via a GUI, which will increase a workload upon the user of the apparatus.

PRIOR ART LITERATURE

Patent Document

Patent Document 1: JP-2010-151707-A

SUMMARY OF THE INVENTION

Problems to be Solved by the Invention

The number of clinical laboratory technicians and other persons who work in clinical practice is confined to a minimum in the stream of medical cost reduction, and every technician who is assigned a plurality of jobs is working under extreme pressure. For this reason, if the technicians can know when they can be away from the apparatus they are in charge of, they could concentrate more on other jobs. As discussed earlier herein, present analyzers can output the time up to the completion of sample-by-sample measurement. For at least patient samples, output of residual time for each sample is a convenient function since displaying the residual time for each sample enables an operator to know scheduled time of reporting to doctors.

The creation of a calibration curve is a job basically during the very busy time of the day immediately before a large quantity of samples is carried to the laboratory. In addition, a plurality of standard solutions (samples) are measured for one item prior to the creation of the calibration curve, and as discussed earlier herein, the standard solutions need to be measured for one item, and a plurality of items may need to be used for one standard solution. With conditions thus changing as needed, it tends to be difficult for the user of the apparatus, for example to know how many more minutes left till the measurement for the item can be started, or to check for failure to set the necessary number of standard solutions in the apparatus or to request the measurement of the standard solutions.

The present invention is intended to enable a user of an analyzer, by minimum operations such as screen operations, to reliably recognize failure to set a reagent used for a desired measurement item or to request the measurement of the item, and accurately understand the time at which the item to be measured can be started. The invention is also intended to enable the user to confirm measurement status information on standard solutions via one GUI screen and thus to efficiently perform assigned jobs.

Means for Solving the Problems

A configuration of the present invention for solving the foregoing problems is outlined below.

The invention is an automatic analyzer provided with a function which, before standard solutions are used to create a calibration curve for measuring a concentration of a constituent contained in a biologically-derived sample such as blood (blood corpuscles or liquid component), urine, and cerebrospinal fluid, outputs measurement status information for each of measurement items (i.e., identification information identifying a measurement status of completed, under process, and prior to process, residual time up to the completion of measurement, and measurement status information on the standard solutions).

More specifically, the automatic analyzer according to the invention includes: a reaction disk with a reaction vessel mounted thereupon for causing a reaction between a first sample and a reagent; a light source that illuminates the reaction vessel with light; a photometer that detects the light passed through the reaction vessel; storage means that receives and then retains calibration curve data used to calculate a concentration of a constituent contained in the first sample; and a control unit that measures the calibration curve data by use of standard solution samples of a known concentration and stores the measured data into the storage means, the control unit further calculating the concentration of the constituent corresponding to a measurement item of the first sample based on information detected by the photometer and the calibration curve data stored in the storage means, wherein when the control unit measures the calibration curve data, the unit outputs measurement status information on the calibration curve data for each measurement item to an information apparatus.

Advantageous Effect of the Invention

The present invention enables a user of the analyzer by minimum operations such as screen operations to reliably recognize failure to set a reagent used for a desired measurement item or to request the measurement of the item, and accurately understand the time at which the item to be measured becomes measurable. The invention also enables the user to confirm measurement status information on standard solutions via one GUI screen and thus to efficiently perform assigned jobs.

BRIEF DESCRIPTION OF THE DRAWINGS

FIG. 2 is a diagram showing an example of GUI screen according to the embodiment;

FIG. 3 is a diagram showing another example of GUI screen according to the embodiment;

FIG. 4 is a diagram showing yet another example of GUI screen according to the embodiment;

FIG. 5 is a diagram showing still another example of GUI screen according to the embodiment;

FIG. 6 is a diagram showing still yet another example of GUI screen according to the embodiment;

FIG. 7 is a diagram showing a further example of GUI screen according to the embodiment;

FIG. 8 is a diagram showing a further example of GUI screen according to the embodiment; and FIG. 9 is a diagram showing a further example of GUI screen according to the embodiment.

MODES FOR CARRYING OUT THE INVENTION

Figure 1:
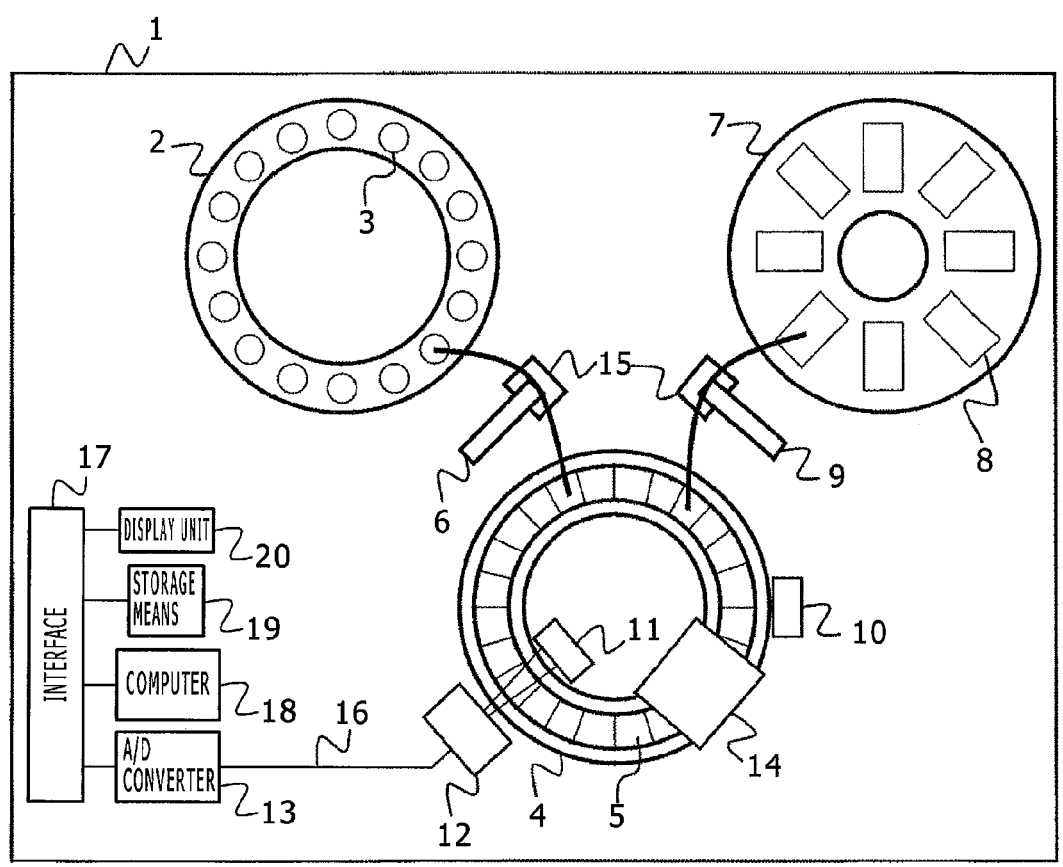
FIG. 1 is a diagram representing a state in which a conceptual diagram of a control system is added to a top layout view of major sections of an automatic analyzer according to an embodiment of the present invention.

Hereunder, an automatic analyzer for clinical laboratory tests according to an embodiment of the present invention, and examples of screen composition and functions of the analyzer will be described using FIGS. 1 to 9.

First, an example of an automatic analyzer the present invention is applied to is described below with FIG. 1 by way of example. FIG. 1 is a diagram representing a state where a conceptual diagram of a control system is added to a top layout view of major sections of the automatic analyzer. The automatic analyzer the invention is intended for includes a mechanism that uses dispenser nozzles to collect a predetermined amount of liquids such as samples and reagents. While an automatic analyzer for clinical laboratory tests, used to analyze such biological samples as of blood and urine, is taken as an example in the following description, a scheme that the analyzer employs to transport a sample to an analyzing unit may be, but is not limited to, a rack transport scheme that uses a rack, for example.

The automatic analyzer 1 includes a samples disk 2, sample containers 3 arranged concentrically thereupon, a reaction disk 4, reaction vessels 5 arranged concentrically on the reaction disk, a sample-dispensing mechanism 6, a reagent disk 7, reagent containers 8 arranged concentrically on the reaction disk and containing various reagents, a reagent-dispensing mechanism 9, a stirring mechanism 10, a light source 11, a photometer (multiwavelength photometer) 12, an A/D converter 13, a reaction vessel cleaning mechanism 14, and a dispenser nozzle cleaning mechanism 15.

The automatic analyzer 1 analyzes a sample in the following sequence. First, the sample-dispensing mechanism 6 dispenses the sample to be analyzed, from a sample container 6 into a reaction vessel 5. Next, the reagent-dispensing mechanism 9 dispenses a reagent to be used for the analysis, from a reagent container 8 into the reaction vessel 5. After this, the stirring mechanism 10 stirs the dispensed sample and reagent to generate a mixture of both liquids. Light that has been emitted from the light source 11 and has passed through the reaction vessel 5 containing the liquid mixture is detected and measured by the photometer (multiwavelength photometer) 12 and then transmitted to an interface 17 via the A/D converter 13. A computer 18 includes a control unit. After measurement results have been computed by the control unit, the obtained measurement results are saved in storage means 19. In addition, the measurement results are output to an information apparatus and, for example, displayed at a display unit 20. The dispenser nozzle cleaning mechanism 15 cleans a tip of a dispenser nozzle whenever the sample-dispensing mechanism 6 and the reagent-dispensing mechanism 9 dispense a sample or reagent. After a reaction between the liquids, the reaction vessel 5 is cleaned by the reaction vessel cleaning mechanism 14 and then used repeatedly for following reactions. These operating mechanisms of the analyzer are all controlled via communication means 16 and the interface 17 by the control unit included in the computer 18.

A calibration curve is used for the computation of the measurement results. The calibration curve data is measured before a sample of an unknown concentration corresponding to a predetermined item is measured. The calibration curve data can be created by using standard solutions of a known concentration which corresponds to the predetermined item and deriving a relationship between the known concentration and the information detected by the photometer. The unknown concentration of the sample that corresponds to the predetermined item is calculated from the photometer-detected information obtained from the above-derived relationship.

More specific examples in which measurement status information on the calibration curve data by the automatic analyzer in the present invention is output to an information apparatus are described below using FIGS. 2 to 9. For the sake of convenience in the description, display details of the measurement status information when the display unit 20 included in the automatic analyzer is the information apparatus are described in FIGS. 2 to 9. The measurement status information, however, does not always need to be output to the display unit 20. Instead of being displayed, the measurement status information may only be output to a printer that prints the information onto a paper medium, a mobile device that displays the information, or any other information apparatus. In other words, advantageous effects of the present invention can be obtained if the measurement status information is output to practically every type of information apparatus using a method which enables an operator to recognize the measurement status information.

FIGS. 2 to 9 show examples of measurement status confirmation information display on the GUI screen, and more specifically, examples in which the creation of a calibration curve (i.e., calibration) takes place using five standard solutions (STD 1 to STD 5) for one measurement item (Test C).

The GUI screen is classified into two major screens. One is a main screen 21 showing each device operation category, and the other is a sub screen 22 showing a detailed status of the main screen. When measurement status information on the standard solutions is displayed in the sub screen 22, a standard solution measurement status for each item display area 24 and a standard solution measurement status of specified item display area 25 for a specific item are displayed in the sub screen 22. The specific item here is an item that has been selected in the area 24.

A present measurement status, item names, locations of reagents, usage conditions of the reagents, execution methods of calibration, and residual time up to the completion of measurement of all standard solutions needed for the item for which the calibration is currently in progress are displayed in the standard solution measurement status for each item display area 24. Either symbol P denoting "Under process," symbol S denoting "Calibration succeeded," or symbol F denoting "Calibration failed" is optionally displayed under "Status" in the measurement status display area 24. This measurement status information, however, needs only to be identification information that enables the operator to discriminate whether the measurement is completed, under process, or has not begun, and the identification information is not limited to S, P, and F. The operator only needs to be able to discriminate the measurement status, for example, by color, hatching, or any other appropriate forms. In the example of FIG. 2, users can identify that measurement is completed when S and P are displayed; the measurement is under process when P is displayed; and the measurement has not begun when no symbol is displayed (blank).

In the standard solution measurement status of specified item display area 25, a present measurement status, names of standard solutions, locations of the standard solutions, analysis start time for each of the standard solutions, and residual time up to the completion of measurement of each standard solution are displayed as standard-solution measurement status information on the item selected in the standard solution measurement status for each item display area 24. In the measurement status display area 25, symbol P, S, or F is optionally displayed under "Status," as in the standard solution measurement status for each item display area 24. This measurement status information, as with what is described above, needs only to be identification information that enables the operator to discriminate whether the measurement is completed, under process, or has not begun.

The example where the standard solution measurement status for each item display area 24 and the standard solution measurement status of specified item display area 25 are displayed on a same screen is described in FIG. 2. The two display areas, however, do not always need to be displayed on a same screen. Instead, the standard solution measurement status for each item display area 24 may be displayed independently on a display screen different from the present display screen by selecting a predetermined item from a list displayed under "Item name" in the standard solution measurement status for each item display area 24. The simultaneous display of the two display areas on a same screen, however, enables more efficient performance of jobs since the measurement status information on the standard solutions can be confirmed in one GUI.

FIG. 2 shows a GUI screen displayed when the measurement of item "Test C" is requested using an all-point calibration executing method. When "Test C" is selected in the standard solution measurement status for each item display area 24, the names and locations of all the five standard solutions necessary for "Test C" are displayed in the standard solution measurement status of specified item display area 25. Standard solution names STD 1 to STD 5 denote the standard solutions each having a different known concentration of the constituent.

FIG. 3 shows a GUI screen displayed when the measurement of item "Test C" is requested using a blank calibration executing method. When "Test C" is selected in the standard solution measurement status for each item display area 24, the name and location of a first standard solution (STD 1) are displayed in the standard solution measurement status of specified item display area 25.

That is to say, even in the same item, the standard solution to be needed will be different when the calibration executing method changes. In order that the standard solution corresponding to the calibration executing method will be displayed in the standard solution measurement status of specified item display area 25, the control unit outputs the measurement status information to the display unit and causes the display unit to display the information.

FIG. 4 shows a GUI screen displayed when the measurement of item "Test C" is requested using the all-point calibration executing method, and the apparatus is activated to start the measurement of up to a third standard solution (STD 3). In this status, since not all standard-solution measurements are completed, nothing is displayed under "Status" and "Residual time" in the standard solution measurement status for each item display area 24. This means that upon visually confirming that nothing is displayed under "Status" and "Residual time," the operator can readily recognize that the corresponding reagent remains unmeasured. When "Test C" is selected in the standard solution measurement status for each item display area 24, "P" is displayed under "Status" for the first, second, and third standard solutions (STD 1, STD 2, STD 3) whose measurement has been started in the standard solution measurement status of specified item display area 25. In addition, time is displayed under each "Analysis start time" and "Residual time". This means that upon visually confirming the display under "Analysis start time" and "Residual time," the operator can readily recognize that a measurement of the corresponding reagent is under process. At the present phase, since not all of the necessary standard-solution measurements are completed, the measurement status information is displayed as "prior to process" identification information under "Status" in the standard solution measurement status for each item display area 24.

FIG. 5 shows a GUI screen displayed when the measurement of item "Test C" is requested using the all-point calibration executing method, and the apparatus is activated to start the measurement of all standard solutions (STD 1-STD 5). In this status, since the measurement of all standard solutions has already begun, "P" is displayed under "Status" in addition to time displayed under "Residual time"

in the standard solution measurement status for each item display area 24. When "Test C" is selected in the standard solution measurement status for each item display area 24, "P" is displayed under "Status" of all the standard solutions in the standard solution measurement status of specified item display area 25. In addition, time is displayed under each "Analysis start time" and "Residual time". The operator can accordingly recognize the residual time up to the completion of the measurement in the all-point calibration executing method for the "Test C" item. The time information displayed under "Residual time" in the standard solution measurement status for each item display area 24 denotes the longest residual time displayed under "Residual time" in the standard solution measurement status of specified item display area 25, and the control unit has already output this residual time to the display unit. Referring to FIG. 5, the residual time for the fifth standard solution (STD 5) corresponds to the output residual time. Hence, "10 min" is displayed as the residual time.

FIG. 6 shows a GUI screen displayed when after the measurement of item "Test C" has been requested using the all-point calibration executing method, although the apparatus is activated to start the measurement of all the standard solutions (STD 1-STD 5), the operator fails to set only the fourth standard solution (STD 4) in place. In this status, since the measurement only of the fourth standard solution (STD 4) is not performed, and normal calibration does not take place, "F" is displayed under "Status" in the standard solution measurement status for each item display area 24, and nothing is displayed under "Residual time." In addition, FIG. 6 unlike FIG. 5 indicates that when "Test C" is selected in the standard solution measurement status for each item display area 24, "F" is displayed under "Status" only of the fourth standard solution (STD 4), in the standard solution measurement status of specified item display area 25, and nothing is displayed under "Analysis start time" and "Residual time." Accordingly, the operator can visually confirm that the calibration for "Test C" has ended but failed. Further, since the space under "Analysis start time" of the fourth standard solution (STD 4) in the standard solution measurement status of specified item display area 25 is blank, the operator can recognize that the analysis of the fourth standard solution has not begun. The display serves as a reminder of failure to set a standard solution and to request the measurement of a test item.

FIG. 7 shows a GUI screen displayed when after the measurement of item "Test C" has been requested using the all-point calibration executing method, although the apparatus is activated to start the measurement of all the standard solutions (STD 1-STD 5), a second measurement of the fourth standard solution (STD 4) is not performed as STD 4 lacks enough quantity. In this status, since only the second measurement of STD 4 is not performed, and normal calibration does not take place, "F" is displayed under "Status" in the standard solution measurement status for each item display area 24, and nothing is displayed under "Residual time." In addition, FIG. 7 unlike FIG. 5 indicates that when "Test C" is selected in the standard solution measurement status for each item display area 24, "F" is displayed under "Status" only for the second measurement of STD 4, in the standard solution measurement status of specified item display area 25, and nothing is displayed under "Analysis start time" and "Residual time." The display serves as a reminder that the fourth standard solution (STD 4) lacks enough quantity.

FIG. 8 shows a GUI screen displayed when the measurement of item "Test C" is requested using the all-point calibration executing method, and the measurement of up to the third standard solution (STD 3) has ended. In this status, since not all the standard-solution measurements are completed, "P" is displayed under "Status" in the standard solution measurement status for each item display area 24, and the longest residual time up to the completion of the measurement is displayed under "Residual time." In addition, when "Test C" is selected in the standard solution measurement status for each item display area 24, "S" is displayed under "Status" for the first, second, and third standard solutions (STD 1, STD 2, STD 3) whose measurement has been completed in the standard solution measurement status of specified item display area 25, and nothing is displayed under "Residual time." Furthermore, "P" is displayed under "Status" for the fourth and fifth standard solutions (STD 4, STD 5) whose measurement is still under process, and residual time up to the completion of the measurement is displayed under "Residual time."

FIG. 9 shows a GUI screen displayed when after the measurement of item "Test C" has been requested using the all-point calibration executing method, measurement of all standard solutions has ended with the success of the calibration. In this status, since the measurement of all standard solutions has already ended, "S" is displayed under "Status" in the standard solution measurement status of each item display area 24, and nothing is displayed under "Residual time." In addition, when "Test C" is selected in the standard solution measurement status of each item display area 24, "S" is displayed under "Status" of all the standard solutions in the standard solution measurement status of specified item display area 25, and nothing is displayed under "Residual time."

The embodiments of the present invention have been described above. The invention enables measurement status information on calibration curve data to be easily confirmed for each measurement item. The invention also enables the user of the apparatus by minimum operations such as screen operations to reliably recognize failure to set a reagent used for a desired measurement item or to request the measurement of the item, and accurately understand the time at which the item to be measured becomes measurable.

In addition, the invention enables the user to confirm the scheduled time for creating a calibration curve for each item, accurately recognize the time to be away from the apparatus, and concentrate on other jobs in spare time, thereby improving job efficiency.

DESCRIPTION OF REFERENCE NUMERALS

1 Automatic analyzer
2 Samples disk
3 Sample container
4 Reaction disk
5 Reaction vessel
6 Sample-dispensing mechanism
7 Reagent disk
8 Reagent container
9 Reagent-dispensing mechanism
10 Stirring mechanism
11 Light source
12 Photometer (Multiwavelength photometer)
13 A/D converter
14 Reaction vessel cleaning mechanism
15 Dispenser nozzle cleaning mechanism
16 Communication means
17 Interface
18 Computer 19 Storage means
20 Display unit
21 Main screen
22 Sub screen
23 Standard-solution measurement status screen tab
24 Standard solution measurement status for each item display area
25 Standard solution measurement status of specified item display area

The invention claimed is:

1. An automatic analyzer comprising:
a reaction disk configured to hold a plurality of first containers each holding standard solutions each having a known concentration, and configured to hold a plurality of second containers each holding reaction solutions of a sample, which includes a constituent to be measured, and a reagent;
a light source that illuminates ones of the first containers and the second containers with light;
a photometer that detects light that has passed through the ones of the first containers and the second containers;
a storage device that stores a plurality of measurement items respectively corresponding to a plurality of constituents of the sample to be measured, calibration curve data corresponding to each of the plurality of measurement items, and identification information for identifying a plurality of the standard solutions necessary for creating the calibration curve data corresponding to each of the plurality of measurement items, the identification of which standard solutions are necessary being based on a calibration method for each of the plurality of measurement items; and
a control unit, coupled to the photometer, storage device, and an information apparatus defined by a display, programmed to:
for each of the plurality of measurement items, instruct the photometer to measure first information for each of the plurality of the standard solutions necessary for creating the calibration curve data that are identified based on the stored identification information,
output measurement status information indicating a measurement status of the calibration curve data for each of the measurement items to the information apparatus while creating the calibration curve data based on the first information and store the measured calibration curve data corresponding to the measurement items into the storage device, the measurement status information including information indicating respective residual waiting times up to completion of measurement for each of the standard solutions necessary for creating the calibration curve data for each of the measurement items and including information indicating respective residual waiting times up to completion of measurement for each of the measurement items, and further including information indicating the calibration method corresponding to each of the measurement items;
upon determination that the measurement of the first information for all of the standard solutions necessary for creating the calibration curve data of one of the measurement items has begun, output the measurement status information which further includes information indicating that the one of the measurement items is under process;
upon selecting one of the measurement items, display on the information apparatus the measurement status information of all of the standard solutions necessary for creating the calibration curve data for the selected one of the measurement items and the measurement status information of each of the plurality of measurement items simultaneously on a same screen of the information apparatus;
upon determination that the measurement of the first information for all of the standard solutions necessary for creating the calibration curve data of one of the measurement items has not begun, output the measurement status information which further includes the identification information indicating that the one of the measurement items which has not begun is prior to process, the information indicating prior to process being a blank space corresponding to the one of the measurement items;
instruct the photometer to measure second information of one of the reaction solutions of the sample and the reagent; and
calculate a concentration of the constituent corresponding to one of the measurement items of the one of the reaction solutions based on the second information detected by the photometer and the calibration curve data stored in the storage device corresponding to the one of the measurement items.

2. The automatic analyzer according to claim 1, wherein the measurement status information further includes identification information identifying one of a measurement status of completed, under process, and prior to process for each of the measurement items; and
wherein the control unit is further programmed to output the identification information for each of the measurement items.

3. The automatic analyzer according to claim 1, wherein the information indicating the respective residual waiting times up to completion of measurement for each of the measurement items corresponds to a longest of the respective residual waiting times up to completion of measurement among all of the standard solutions necessary for creating the respective calibration curve data thereof.

4. The automatic analyzer according to claim 2, wherein the control unit is further programmed to, for all of the standard solutions necessary for creating the calibration curve data for the selected measurement items, output identification information indicating a completed state, an ongoing state, and an unexecuted state of measurement for each of the standard solutions.

5. The automatic analyzer according to claim 1, wherein the display may be a mobile device that displays the measurement status information.

6. The automatic analyzer corresponding to claim 1,
wherein the measurement of the first information for all of the standard solutions necessary for creating the calibration curve data of one of the measurement items has not begun is a case that measurement of the first information for at least one of all of the standard solutions necessary for creating the calibration curve data of one of the measurement items has not begun.

7. The automatic analyzer corresponding to claim 1,
wherein the control unit is further programmed to:
output the measurement status information which further includes identification information indicating one of prior to process and under process for each of all of the standard solutions necessary for creating the calibration curve data of the selected one of the measurement items.

* * * * *